United States Patent [19]
del Valle et al.

[11] Patent Number: 6,091,015
[45] Date of Patent: Jul. 18, 2000

[54] PHOTOVOLTAIC ENERGY SUPPLY SYSTEM WITH OPTICAL FIBER FOR IMPLANTABLE MEDICAL DEVICES

[75] Inventors: Carlos Algora del Valle, Madrid; Luis Castañer Muñoz, Barcelona, both of Spain

[73] Assignee: Universidad Politécnica de Cataluña, Barcelona, Spain

[21] Appl. No.: 09/085,455

[22] Filed: May 28, 1998

[30]     Foreign Application Priority Data

May 28, 1997 [ES] Spain ..................................... 9701150

[51] Int. Cl.⁷ ............................. H01L 25/00; A61B 17/36
[52] U.S. Cl. ............................ 136/243; 136/291; 606/15; 606/22; 607/95
[58] Field of Search ..................................... 136/243, 291; 606/15, 22; 607/95

[56]     References Cited

U.S. PATENT DOCUMENTS

| | | | |
|---|---|---|---|
| 4,432,363 | 2/1984 | Kakegawa | 128/419 PS |
| 4,900,303 | 2/1990 | Lemelson | 604/54 |
| 5,599,317 | 2/1997 | Hauser | 604/256 |

*Primary Examiner*—Mark Chapman
*Attorney, Agent, or Firm*—Clark & Brody

[57]     ABSTRACT

An energy supply system for implantable medical devices generates an energy supply by a photovoltaic converter which transforms the light coming from outside of the body. The light is carried to the converter by an optical fiber. This system allows the implanted devices to work without the time restrictions of batteries and opens the door to the development of new devices with much higher power ratings. The system includes a light source (1) external to the patient's body, an optical fiber (3) which runs from a point on the surface of the patient to the implantable device (4) and a photovoltaic converter (5) placed inside the device where the optical fiber ends. Finally, a power conditioning stage (6) ensures that the electrical power generated suits the needs of the other components (7) of the implantable device.

14 Claims, 2 Drawing Sheets

PHOTOVOLTAIC ENERGY SUPPLY SYSTEM WITH OPTICAL FIBER FOR IMPLANTABLE MEDICAL DEVICES

TECHNICAL FIELD

An energy supply system for implantable medical devices is described. The energy supply is produced by the electricity generated by a photovoltaic converter transforming light coming through an optical fiber from the outside of the body. This allows the extended use of the implanted medical devices without energy restrictions.

BACKGROUND

Today, an increasing number of illnesses and dysfunctions are corrected or controlled by the implantation into the body of devices. Examples are the common pacemaker, the anti-tachycardia pacemaker and the automatic implantable defibrillator, which are designed to correct irregularities such as tachycardia, or ventricular or auricular fibrillation. Other devices are currently under research or development, or will be in the future, such as drug infusion pumps, pain relief stimulators or implantable artificial hearts and kidneys.

Very significant progress has been made in the functionality of implantable devices, along with size reduction and increase in longevity, as a result of advances in batteries, circuits and technology.

Basically, an implantable device is composed of a) an actuator, performing the physical function, and b) a control electronics of the actuator as well as of the other auxiliary elements all requiring energy (generally electric) supplied by a battery.

Nickel-cadmium and zinc-mercury batteries were used to supply the first generations of implantable devices, but their large size and short life span made nuclear batteries a potential option soon disregarded due to the very strict regulations applying to them. Since then, lithium batteries have become those most used because of their longer duration, comparable to the nuclear cells but subject to less stringent regulations. Additionally, lithium batteries offered several advantages such as a discharge indicator, no internal current leakage (self-discharge), and lack of gaseous emissions. This provides conditions for more reliable performance.

Even if the improvements in longevity are taken into account, the concept of battery is still that of a receptacle containing a limited amount of energy which runs out after a certain amount of time has elapsed. In the case of implantable medical devices this fact leads to three situations:

a) Replacement of the exhausted batteries (more precisely, replacement of the whole implantable device which is hermetically sealed), with a new set. This replacement is carried out by means of surgical intervention, which in some cases exposes the patients to some risks, as well as substantial costs to the health-care system, contrary to the worldwide trend of reducing medical costs.

b) Limitation on the potential for today's implantable devices. In fact, the evolution of the technology in implantable medical devices has drastically reduced the energy requirements of the actuator, making the enhancement and extension of the device's functionality for a given battery capacity possible. Among the possible uses for the energy saved from more efficient actuators, trends point towards its use in increased automation, and the incorporation of distant diagnosis and monitoring by telemetry. As an example, in today's common pacemakers, 50% to 65% of the energy is devoted to these additional functions with predictions of a rise to 95% in the near future.

However, if the energy saved from enhanced efficiency of the actuator is to be used in increased functionality, other not less attractive possibilities, such as the increase in the battery lifetime, or the reduction in the battery size, may be out of scope (as the battery takes up the biggest part of the whole device, if battery size were reduced the size of the whole device would be miniaturized as well). Therefore, a trade-off appears between the different options available for using the extra energy saved by the actuators, but not all of these options can be considered simultaneously.

c) Stagnation in new developments in medical implantable devices, requiring a much larger amount of energy than devices available today. The only possible way with present technologies, is to oversize the batteries (in energy, and consequently in physical dimensions), or to reduce the usable time. This is the case in the implantable defibrillator, whose operational principle requires a high voltage, drawing a large amount of energy every time it is actuated. The typical lifetime of these devices is 2 to 3 years. Other examples such as the artificial implantable heart requiring an extremely large amount of energy, are not viable using present technologies and batteries.

SUMMARY OF THE INVENTION

It then becomes clear that a new procedure is needed to solve the three aforementioned problems. Therefore, the basic idea behind this invention is to provide a permanent source of energy (in terms of patient lifetime or device lifetime) for an implantable device.

The way this works is as follows: light coming from outside the patient enters one end of an optical fiber that has been installed into the patient. The light travels inside the fiber until it reaches a photovoltaic converter placed at the other end, inside the patient. This converter transforms the light directly into electricity, which is conditioned by an electronic circuit either to supply electric power to the elements of the device or to charge an accumulator. As a result, the system provides a permanent energy supply to the implanted device through the optical fiber. This arrangement leads to:

permanent performance, availability of energy levels high enough to supply devices with increased functionality, or future devices requiring a much larger amount of energy, and miniaturization of the system due to large batteries not being required to keep the device operational for many years.

On the other hand, the following disadvantages can be foreseen from the medical point of view:

potential rejection from the patient's body of the optical fiber placed permanently inside, and potential infection because one of the ends of the optical fiber arrives to the patient's surface thus becoming a potential entry point for infection.

Fortunately, these two drawbacks of the system proposed here, do not present real problems because:

Optical fiber is a biocompatible material, made of inert plastics (of medical grade) which have already been successfully used in other medical applications, and Optical fibers have very small diameters, several tens of microns in diameter, (similar to that of a human hair). Therefore, the end of the fiber close to the skin would be sealed by natural means (epithelialization). This is a situation already solved in other medical applications, such as internal hypodermic reservoirs and pumps for analgesic drugs.

The system proposed here, although being of general use for any medical implanted device, can be used with several variations specially those related to the type of light coupled to the optical fiber. For instance, ambient light could be used in such a way that the energy supply would be weak but almost permanent. Other sources could also be used such as laser, LED, or incandescent bulb light where much more energy could be supplied per unit of time but less frequently. This "direct" connection between an artificial light source and the optical fiber opens up the possibility of using the same fiber (or a second one) also to transmit data from inside the body to the outside thus making it possible to transmit information on the system's performance as well as the state of the patient. In this way, the proposed system exchanges energy and information between patient and the outside. Therefore, the proposed system uses a unidirectional flow of energy (from the outside to the inside) and a bidirectional flow of information between the inside and the outside.

Another interesting possibility for this is that it could be a 'central energy unit' able to power several implantable devices once the light is converted into electricity. This allows patients requiring more than one implantable device to need just one fiber connection to the skin.

DETAILED DESCRIPTION OF THE PREFERRED EMBODIMENT

Figure 1:
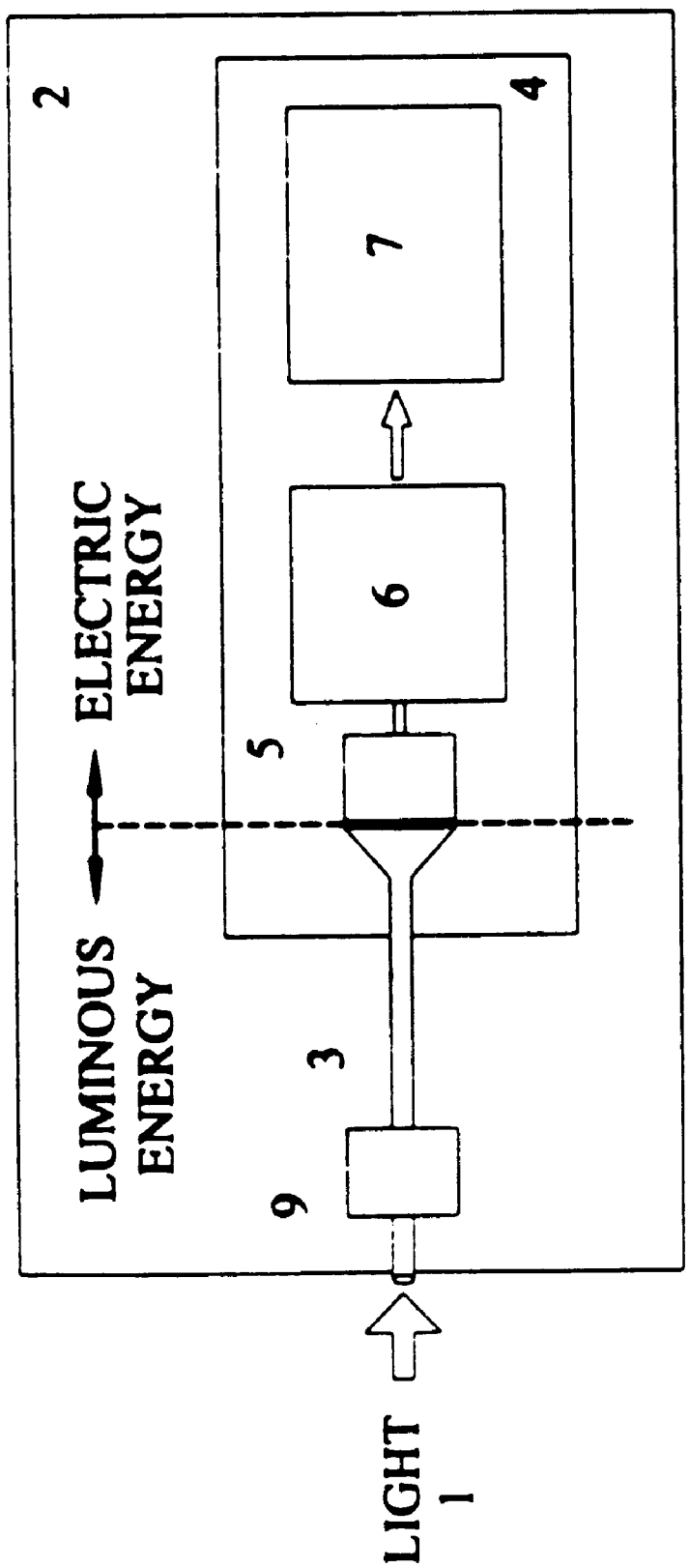
FIG. 1 is a schematic diagram of a system in accordance with the invention

With reference to FIG. 1, the proposed system is made up of a light source (1) outside of patient's body (2), an optical fiber (3) running from a point on the surface of the patient's body to the implantable device (4), a photovoltaic converter (5) placed inside the device to which the optical fiber is connected. Finally, a power conditioning circuit (6) adapts the electrical power generated by the photovoltaic converter to the levels required by the other elements (7) of the implanted device (see FIG. 1).

Figure 2:
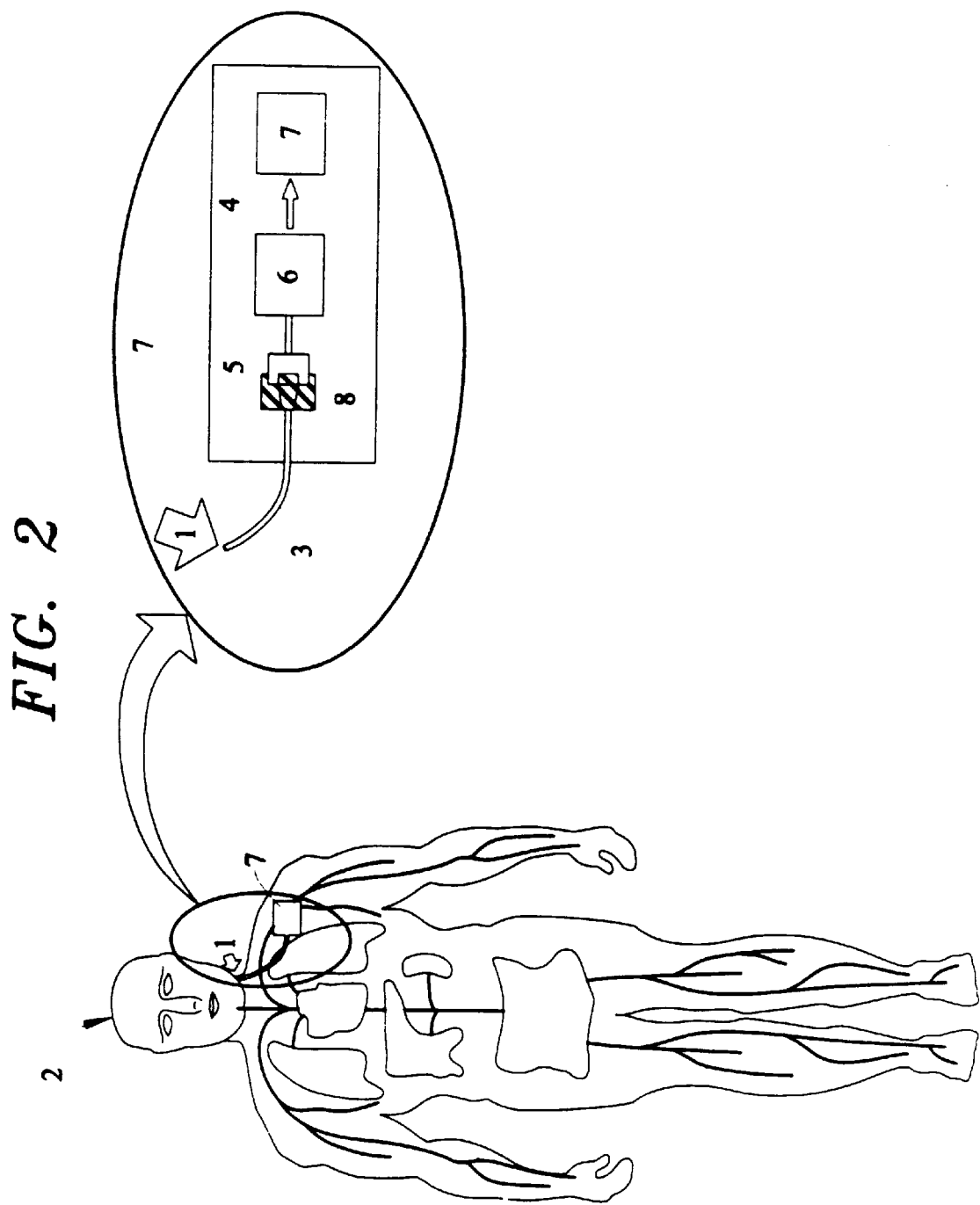
FIG. 2 is a schematic diagram showing installation of the system of FIG. 1 in a human body.

Among the several possible ways of manufacturing this system (7) one is shown in FIG. 2. The photovoltaic converter (5) will be placed inside the implantable device (4). Its electric terminals will be connected to a power conditioner (6) adapting the voltage and current levels to the requirements of the other conventional elements (7). Conventional elements are understood as those already used in non-photovoltaically powered implantable devices. The photovoltaic converter would have a connector (8) in order to make an efficient link with the optical fiber. From the connector the optical fiber (3) will run a short distance inside the implantable device before coming out of the device thus being the only element inside the human body (2) until it reaches the epidermis at a specific place were the light can enter (1). If ambient light is to be used, the external point should be chosen to provide maximum exposure such as the hands, neck, ears, etc. In case other guided light sources are used, any place could be used depending on patient comfort. The size of the converter, manufacturing material, diameter of the optical fiber and light wavelength should be chosen according to the energy supply required by the implantable device, meaning that the power requirements of the device are the most important aspect of the total system.

The arrangements aforementioned could be modified, provided the main operating principle is maintained, such as the inclusion of optics or optical connectors and the electro-optical devices such as that shown at (9) required to modify the transmission of energy and information. In addition, to the medical applications, others such as veterinarian and biological uses are envisaged, provided they follow the same principle here described.

Modifications within the scope of the appended claims will be apparent to those of skill in the art.

We claim:

1. A photovoltaic energy supply system for an implantable medical device comprising very thin optical fiber of biocompatible material for being implanted into a living body and sealed at one end to the skin of said body by epithelialization, and a photovoltaic converter connected to the opposite end of said fiber for transforming ambient light from the outside of the body and passing through said optical fiber into electric power for said medical device, a power conditioning stage at the output of the photovoltaic converter, means for modifying said power for use by said device, and means for sending information from the implanted device to monitor the state and function of the system or of the patient.

2. A system according to claim 1 further comprising a plurality of said medical devices for being implanted in different parts of the body and wherein said converter provides power for said several devices.

3. A system according to claim 2 further comprising an artificial light source for generating said light.

4. A system according to claim 2 further comprising means for modifying said light transmitted through said fiber.

5. A system according to claim 1 further comprising an artificial light source for generating said light.

6. A system according to claim 1 further comprising means for modifying said light transmitted through said fiber.

7. A system according to claim 1 wherein said body is a human body.

8. An energy supply system according to claim 1 wherein said very thin optical fiber has a diameter of several tens of microns.

9. A method of providing energy to at least one medical device implanted in a living body comprising the steps of:

implanting in said living body at least one optical fiber made of biologically compatible material having a maximum outer diameter on the order of several tens of microns, providing a photovoltaic converter at an output end of said optical fiber, operatively connecting said photovoltaic converter to said medical device, and placing an input end of said optical fiber in the skin of said body such that it is sealed thereto by epithelialization.

10. A method according to claim 9 wherein said step of placing further comprises the step of locating said input end at a location on said body generally exposed to ambient light.

11. A method according to claim 10 wherein said location in is a portion of said body selected from the group consisting of a hand, the neck, and an ear.

12. A method according to claim 9 wherein said step of operatively connecting said photovoltaic converter to said medical device comprises connecting said photovoltaic converter to a plurality of medical devices.

13. A method according to claim 9 wherein said photovoltaic converter is capable of receiving information through said optical fiber and transmitting information through said optical fiber.

14. A method according to claim 9 wherein said input end is located on the surface of said body.

* * * * *

UNITED STATES PATENT AND TRADEMARK OFFICE
CERTIFICATE OF CORRECTION

PATENT NO. : 6,091,015
DATED : July 18, 2000
INVENTOR(S) : Carlos Algora del Valle and Luis Castaner Munoz It is certified that error appears in the above-identified patent and that said Letters Patent is hereby corrected as shown below:

Assignees:  Universidad Politécnica de Cataluña, Barcelona, Spain
Universidad Politécnica de Madrid, Madrid, Spain Signed and Sealed this Twenty-ninth Day of May, 2001

*Attest:*

NICHOLAS P. GODICI

*Attesting Officer*  Acting Director of the United States Patent and Trademark Office